United States Patent [19]

Horovitz

[11] Patent Number: 5,032,578
[45] Date of Patent: Jul. 16, 1991

[54] METHOD FOR PREVENTING OR TREATING DEPRESSION EMPLOYING A COMBINATION OF AN ACE INHIBITOR AND A DRUG THAT ACTS AT SEROTONIN RECEPTORS

[75] Inventor: Zola P. Horovitz, Princeton, N.J.

[73] Assignee: E. R. Squibb & Sons, Inc., Princeton, N.J.

[21] Appl. No.: 583,752

[22] Filed: Sep. 17, 1990

[51] Int. Cl.$^5$ .................. A61K 31/40; A61K 31/675; A61K 37/02

[52] U.S. Cl. ......................................... 514/19; 514/7; 514/89; 514/91; 514/92; 514/94; 514/171; 514/212; 514/218; 514/223.5; 514/249; 514/255; 514/278; 514/318; 514/338; 514/343; 514/409; 514/422; 514/423; 514/616; 514/693

[58] Field of Search .................... 514/7, 19, 89, 91, 92, 514/94, 171, 212, 218, 223.5, 249, 255, 278, 318, 338, 343, 409, 422, 423, 616, 693

[56] References Cited

U.S. PATENT DOCUMENTS

| | | | |
|---|---|---|---|
| 4,046,889 | 9/1977 | Ondetti et al. | 514/422 |
| 4,311,697 | 1/1982 | Krapcho | 514/17 |
| 4,311,705 | 1/1982 | Ondetti et al. | 514/422 |
| 4,316,906 | 2/1982 | Ondetti et al. | 514/422 |
| 4,337,201 | 6/1982 | Petrillo, Jr. | 548/413 |
| 4,379,146 | 4/1983 | Greenlee et al. | 548/413 |
| 4,381,297 | 4/1983 | Karanewsky et al. | 548/413 |
| 4,452,790 | 6/1984 | Karanewsky et al. | 546/22 |
| 4,602,002 | 7/1986 | Patchett et al. | 514/11 |
| 4,912,096 | 3/1990 | Sudilovsky | 514/91 |
| 4,931,430 | 6/1990 | Sudilovsky et al. | 514/19 |

FOREIGN PATENT DOCUMENTS

0288907A2 3/1990 European Pat. Off. .
3610391A1 5/1986 Fed. Rep. of Germany .

OTHER PUBLICATIONS

Costall et al (1989), "The Effects of ACE Inhibitors Captopril and SO29,852 in Rodent Tests of Cognition," Pharmacol. Biochem. Behav. 33; 573–579.
Barnes, J. M. et al (1990), "The Effects of Ondansetron, 5-HT$_3$ Receptor Antagonist, on Cognition in Rodents and Primates," Pharmacol. Biochem. Behav. (35; 955–961.
Sudilovsky et al, "Captopril Delays Extinction of Conditional Avoidance Response in the Rat," Poster Presentation, 14th Congress of the Collegium Internationale Neuro-Psychopharmacologicum, Florence, Italy, Jun. 1984.
"Angiotensin Converting Enzyme Inhibitors: Animal Experiments Suggest a New Pharmacological Treatment for Alcohol Abuse in Human," G. Spinosa et al, Alcoholism: Clinical and Experimental Research, vol. 12, No. 1, Jan./Feb. 1988, pp. 65–70.
"Alcohol Satiety, Hypertension and the Renin–Angiotensis System," L. A. Grupp, Medical Hypotheses (1987) 24, 11–19 (Longman Group UK Ltd 1987).
Melo, J. C. et al, J. Pharmacol., 193:1–9 (1975).
Morgan, J. M. et al, Science, 196:87–89 (1977).
Koller, M. et al, Neuroscience Letters, 14:71–75 (1979).
Evered, M. D., Europ. J. Pharmacol., 68:443–449 (1980).
Marson, O. et al, Brazil. J. Med. Biol. Res., 14:73–76 (1981).
Arregui, A. et al, J. Neurochem., 103:1490–1492 (1982).
Scholkens, B. A. et al, Clin. Exper. Hyper.-Theor. Pract., A5:1301–1317 (1983).
Mann, J. F. E. et al, Clin. Sci., 56:585–589 (1979).
Vollmer R. R. et al, Europ. J. Pharmacol., 45:117–125 (1977).
Croog et al, "The Effects of Antihypertensive Therapy on the Quality of Life," New England Journal of Medicine, 314:1657–1664 (Jun. 26), 1986.
Sudilovsky et al, "The Effects of Zofenopril, Captopril and Methyldopa on Shuttle Avoidance Response Extinction in Rats," Poster Presentation, 15th Congress of the Collegium Internationale Neuro-Psychopharmacologicum, San Jaun, Puerto Rico, Dec. 1986.
Sudilovsky et al, "Differential Effects of Captopril, Methyldopa and Propranolol on Cognitive Functioning of Hypertensive Patients," Poster Presentation, 25th Annual Meeting of the American College of Neuropsychopharmacology, Wash., D.C., Dec. '86.
Deicken, R. F., "Captopril Treatment of Depression," Biol. Psychiatry, 1986; 21:1425–1428.
Zubenko, G. S., "Mood-Elevating Effect of Captopril in Depressed Patients," Am. J. Psychiatry, 141:110–11, 1984.
Germain, L. et al, "Treatment of Recurrent Unipolar Major Depression with Captopril," Biol. Psychiatry, 1988; 23:637–641.
Giardina, W. J. et al, "Positive Effects of Captopril in the Behavioral Despair Swim Test," Biol. Psychiatry, 1989; 25:695–702.
Bosio, A. et al, "Antidepressant Activity of ACE-Inhibitors," TIPS, vol. 8, pp. 329–330, 1987 (Abstracts of 141st Annual Meeting of the American Psychiatric Association, Montreal, Canada, May 7–12, 1988.
Buspirone (PDR, 1990, p. 1308).

Primary Examiner—Lester L. Lee
Attorney, Agent, or Firm—Burton Rodney

[57] ABSTRACT

A method is provided for inhibiting onset of or treating depression by administering an ACE inhibitor, such as captopril, fosinopril, zofenopril or ceranapril in combination with a drug that acts at serotonin receptors such as zacopride, over a prolonged period of treatment.

14 Claims, No Drawings

METHOD FOR PREVENTING OR TREATING DEPRESSION EMPLOYING A COMBINATION OF AN ACE INHIBITOR AND A DRUG THAT ACTS AT SEROTONIN RECEPTORS

FIELD OF THE INVENTION

The present invention relates to a method for inhibiting onset of or treating depression employing an angiotensin converting enzyme (ACE) inhibitor such as captopril, SQ 29,852, zofenopril, fosinopril or enalapril, in combination with a drug that interacts with serotonin receptors in the brain, such as zacopride.

BACKGROUND OF THE INVENTION

U.S. Pat. No. 4,912,096 to Sudilovsky discloses a method for preventing or treating depression employing an angiotensin converting enzyme inhibitor which is ceranapril (SQ29,852), zofenopril or fosinopril.

The use of captopril, an angiotensin-converting enzyme inhibitor, for treating depression is disclosed in the following references:

Deicken, R. F., "Captopril Treatment of Depression," Biol. Psychiatry, 1986; 21:1425-1428;

Zubenko, G. S., "Mood-Elevating Effect of Captopril in Depressed Patients," Am. J. Psychiatry 141:110-11, 1984;

Germain, L. et al, "Treatment of Recurrent Unipolar Major Depression with Captopril," Biol Psychiatry, 1988; 23:637-641;

Giardina, W. J. et al, "Positive Effects of Captopril in the Behavioral Despair Swim Test," Biol. Psychiatry, 1989; 25:695-702;

Bosio, A. et al, "Antidepressant Activity of ACE-Inhibitors," TIPS, Vol. 8, pp 329-330, 1987 (Abstracts of 141st Annual Meeting of the American Psychiatric Association, Montreal, Canada, May 7-12, 1988), discloses that captopril has antidepressant activity while enalapril does not. "These results indicate that ACE inhibitor activity is not related to psychotropic effect . . ."

U.S. Pat. Nos. 4,046,889 and 4,105,776 to Ondetti et al discloses proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al, discloses phosphonate substituted amino or imino acids and salts thereof and covers (S)-1-[6-amino-2[-[hydroxy(4-phenylbutyl)-phosphinyl]oxy]-1-oxohexyl]-L-proline (ceranapril, SQ 29,852). These compounds are ACE inhibitors useful in treating hypertension.

U.S. Pat. No. 4,316,960 to Ondetti et al, discloses ether and thioether mercaptoacyl prolines which are ACE inhibitors useful in treating hypertension. This Ondetti et al patent covers zofenopril U.S. Pat. No. 4,931,430 to Sudilovsky et al, discloses a method for preventing or treating anxiety employing an ACE inhibitor in combination with a calcium channel blocker.

Angiotensin converting enzyme inhibitors and 5-HT$_3$ (5-hydroxytryptamine$_3$) receptor antagonists have previously been shown to improve the basal performance of laboratory animals in habituation paradigms and also to overcome the impairment induced by scopolamine (Costall et al (1989), "The effects of ACE inhibitors captopril and SQ29,852 in rodent tests of cognition." Pharmacol. Biochem. Behav. 33; 573-579; Barnes, J. M., et al (1990), "The effects of ondansetron, 5-HT$_3$ receptor antagonist, on cognition in rodents and primates." Pharmacol. Biochem. Behav. (35; 955-961).

Buspirone, a drug that interacts with serotonin receptors in the brain, is known for its use in treating anxiety (PDR, 1990, p. 1308).

Zacopride which also interacts with serotonin receptors in the brain, is known for its use as an anti-emetic.

DESCRIPTION OF THE INVENTION

In accordance with the present invention, a method is provided for preventing or treating depression in mammalian species, over a prolonged period, wherein a combination of an antidepressive effective amount of an angiotensin converting enzyme inhibitor and a drug that interacts with serotonin receptors in the brain, is systemically, such as orally or parenterally, administered over a prolonged period, to inhibit onset of or treat depression during such period "Drugs that interact with serotonin receptors in the brain" and as such are employed in the method of the invention will hereinafter be referred to as "drugs that act at serotonin receptors." These drugs may or may not be 5-HT$_3$ antagonists.

The term "depression" as used herein is as defined in "A Quick Reference to Diagnostic Criteria from DSM-III-R, June, 1987," (American Psychiatric Association), and includes depressive disorders such as dysthymia (depressive neurosis), including primary and secondary types, major depression, and depressive disorder not otherwise specified, as well as bipolar disorders including bipolar disorder, mixed (manic and major depressive episodes), bipolar disorder, depressed, and bipolar disorder not otherwise specified.

With respect to the combination of ACE inhibitor and a drug that acts at serotonin receptors in accordance with the present invention, the ACE inhibitor will be employed in a weight ratio to the drug that acts at serotonin receptors of within the range of from about 0.0005:1 to about $1 \times 10^7$:1 and preferably from about 0.002:1 to about $25 \times 10^4$:1

The angiotensin converting enzyme inhibitor which may be employed herein includes substituted proline derivatives, such as any of those disclosed in U.S. Pat. No. 4,046,889 or 4,105,776 to Ondetti et al mentioned above, with captopril, that is, 1-[(2S)-3-mercapto-2-methylpropionyl]-L-proline, being preferred, carboxyalkyl dipeptide derivatives, such as any of those disclosed in U.S. Pat. No. 4,374,829 mentioned above, with N-(1-ethoxycarbonyl-3-phenylpropyl)-L-alanyl-L-proline, that is, enalapril, being preferred.

Other examples of angiotensin converting enzyme inhibitors suitable for use herein include any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline (ceranapril, SQ 29,852) being preferred, phosphinylalkanoyl prolines disclosed in U.S. Pat. No. 4,168,267 mentioned above with fosinopril being preferred, mercaptoacyl derivatives of substituted prolines, disclosed in U.S. Pat. No. 4,316,906 with zofenopril being preferred, any of the phosphinylalkanoyl substituted prolines disclosed in U.S. Pat. No. 4,337,201 discussed above, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-(1-ethoxycarbonyl-3-phenyl-(lS)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(lS)-5-amino-1-carboxypentyl]amino]-2,3,4,5-tetrahydro-2-oxo-lH-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 Hoechst) disclosed in Arzneimittelforschung 35:1254 (1985), cilazapril (Hoffman-LaRoche) disclosed in J. Cardiovasc. Pharmacol. 9:39 (1987); Ro 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxy-carbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 6:394 (1983).

Preferred are those ACE inhibitors which are proline or substituted proline derivatives, especially ceranapril, captopril, zofenopril and fosinopril.

The above-mentioned U.S. patents are incorporated herein by reference.

The drug that acts at serotonin receptors suitable for use herein may be zacopride (benzamide zacopride), 3α-tropanyl-lH-indole-3-carboxylic acid ester (ICS 205930, Sandoz); [endo]N-(9-methyl-9-azabicyclo-[3,3,1]-non-3-yl)-1-methyl-lH-indazole-3-carboxamide hydrochloride (BRL 43694, Granisetron, Beecham); (1αH,3α,5αH-tropan-3-yl-3,5-dichlorobenzoate (MDL 7222, Merrell Dow); ondansetron; buspirone; and ritanserin.

A preferred combination in accordance with the present invention is ceranapril and zacopride.

In carrying out the method of the present invention, the angiotensin converting enzyme inhibitor in combination with the drug that acts at serotonin receptors may be administered to mammalian species, such as monkeys, dogs, cats, rats and humans, and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidant (ascorbic acid or sodium bisulfite) or the like. Oral dosage forms are preferred, although parenteral forms such as intramuscular, intraperitoneal, or intravenous are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.005 mg/kg to about 100 mg/kg and preferably from about 0.01 mg/kg to about 25 mg/kg, in combination with the drug that acts at serotonin receptors in an amount within the range of from about 0.010 $\mu$g/kg to about 10 mg/kg and preferably from about 0.1 $\mu$g/kg to about 5 mg/kg, with the ACE inhibitor and drug that acts at serotonin receptors being employed together in the same oral dosage form or in separate oral dosage forms taken at the same time.

A preferred oral dosage form, such as tablets or capsules, will contain the ACE inhibitor in an amount of from about 0.1 to about 500 mg, preferably from about 5 to about 200 mg, and more preferably from about 25 to about 150 mg, with the drug that acts at serotonin receptors in an amount of from about 1 $\mu$g to about 200 mg, preferably from about 5 $\mu$g to about 150 mg, and more preferably from about 10 $\mu$g to about 100 mg.

For parenteral administration, the ACE inhibitor will be employed in an amount within the range of from about 0.005 mg/kg to about 10 mg/kg and preferably from about 0.01 mg/kg to about 1 mg/kg, and the drug that acts at serotonin receptors will be employed in an amount within the range of from about 0.005 $\mu$g/kg to about 20 mg/kg and preferably from about 0.01 $\mu$g/kg to about 10 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonfuls.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of ACE inhibitor and drug that acts at serotonin receptors are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as inhibition of onset of or treatment of depression is to continue. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLE 1

An injectable solution for use in inhibiting onset of or treating depression is produced as follows:

| Ceranapril (SQ29,852) | 500 mg |
| Methyl paraben | 5 mg |
| Propyl paraben | 1 mg |
| Sodium chloride | 25 g |
| Water for injection qs. | 5 l. |

The SQ29,852, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 mL of solution in a concentration of 0.5 mg of active ingredient per mL of solution for injection.

A zacopride injectable solution for use in combination with ceranapril for treating or inhibiting onset of depression is prepared as described above except 100 mg zacopride is employed in place of ceranapril.

The so-prepared injectable solutions may be administered separately or as a single injection to prevent or treat depression.

EXAMPLE 2

Two piece #1 gelatin capsules each containing 100 mg of ceranapril are filled with a mixture of the following ingredients:

| Ceranapril | 100 mg |
| Zacopride | 1 mg |
| Magnesium stearate | 7 mg |
| USP lactose | 193 mg. |

The resulting capsules are useful in inhibiting onset of or treating depression.

EXAMPLE 3

A captopril formulation suitable for oral administration for use in combination with a 5-HT$_3$ antagonist in inhibiting onset of or treating depression is set out below.

1000 tablets each containing 100 mg of 1-[(2S)-3-mercapto-2-methylpropionyl]-L-proline were produced from the following ingredients.

| 1-[(2S)-3-Mercapto-2-methylpropionyl]-L-proline (captopril) | 100 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 0.5 mg of active ingredient which together with the drug that acts at serotonin receptors ICS 250930 (5-HT$_3$ antagonist) is used for inhibiting onset of or treating depression.

The ICS 250930 (3α-tropanyl-1H-indole-3-carboxylic acid ester) is formulated as 100 mg tablets as described above with respect to captopril.

The captopril tablets and ICS 250930 tablets may be administered to inhibit onset of or to treat depression.

EXAMPLE 4

By substituting 100 g of 1-(3-mercapto-2-D-methylpropanoyl)-L-proline for the captopril in Example 3 and adding 100 mg Granisetron, 1000 tablets each containing 100 mg of the 1-(3-mercapto-2-D-methylpropanoyl)-L-proline and 1 mg Granisetron are produced which are useful in inhibiting onset of or treating depression.

EXAMPLE 5

1000 tablets each containing 50 mg of fosinopril and 0.5 mg MDL f72222 (1αH,3α,5αH-tropan-3-yl-3,5-dichlorobenzoate) are produced from the following ingredients:

| Fosinopril | 50 g |
| MDL 72222 | 0.5 g |
| Lactose | 100 g |
| Avicel | 150 g |

| | |
|---|---|
| -continued | |
| Corn starch | 50 g |
| Magnesium stearate | 5 g |

The fosinopril, MDL 72222, lactose and Avicel are admixed, then blended with the corn starch. Magnesium stearate is added. The dry mixture is compressed in a tablet press to form 1000 505 mg tablets each containing 50.5 mg of active ingredients. The tablets are coated with a solution of Methocel E 15 (methyl cellulose) including as a color a lake containing yellow #6. The resulting tablets are useful in inhibiting onset of or treating depression.

EXAMPLE 6

Two piece #1 gelatin capsules each containing 100 mg of enalapril and 100 mg zacopride are filled with a mixture of the following ingredients:

| | |
|---|---|
| Enalapril | 100 mg |
| Zacopride | 0.1 mg |
| Magnesium stearate | 7 mg |
| USP lactose | 193 mg. |

The resulting capsules are useful in inhibiting onset of or treating depression.

What is claimed is:

1. A method for inhibiting onset of or treating depression in a mammalian specie, which comprises administering to a mammalian specie in need of such treatment an antidepressive effective amount of a combination of an angiotensin converting enzyme (ACE) inhibitor with a drug that acts at serotonin receptors, in a weight ratio of said ACE inhibitor to said drug that acts at serotonin receptors of within the range of from about 0.0005:1 to about $1 \times 10^7$:1, wherein the drug that acts at serotonin receptors is zacopride; 3α-tropanyl-1H-indole-3-carboxylic acid ester; N-(9-methyl-9-azabicyclo-non-3-yl)-1-methyl-1H-indazole-3-carboxyamide; 1αH, 3α, 50αH-tropan-3-yl-3,5-dichlorobenzoate; ondansetron; buspirone or ritanserin.

2. The method as defined in claim 1 wherein the angiotensin converting enzyme inhibitor is a phosphonate substituted amino or imino acid or salt thereof, a proline derivative, a substituted proline derivative, a carboxyalkyl dipeptide derivative, a phosphinylalkanoyl proline derivative or a phosphonamidate derivative.

3. The method as defined in claim 1 wherein said angiotensin converting enzyme inhibitor is a proline derivative or a substituted proline derivative.

4. The method as defined in claim 1 wherein said angiotensin converting enzyme inhibitor is a carboxyalkyl dipeptide derivative.

5. The method as defined in claim 1 wherein said angiotensin converting enzyme inhibitor is a phosphinylalkanoyl proline derivative, a phosphoramidate derivative, or a phosphonate substituted amino or imino acid or salt thereof.

6. The method as defined in claim 1 wherein said angiotensin converting enzyme inhibitor is captopril.

7. The method as defined in claim 1 wherein said angiotensin converting enzyme inhibitor is enalapril or lisinopril.

8. The method as defined in claim 1 wherein said angiotensin converting enzyme inhibitor is zofenopril or fosinopril.

9. The method as defined in claim 1 wherein said angiotensin converting enzyme inhibitor is (S)-1-L-proline (ceranapril).

10. The method as defined in claim 1 wherein the drug that acts at serotonin receptors is zacopride or buspirone.

11. The method as defined in claim 1 wherein the drug that acts at serotonin receptors is zacopride.

12. The method as defined in claim 1 wherein the ACE inhibitor is ceranapril and the drug that acts at serotonin receptors is zacopride.

13. The method as defined in claim 1 wherein said angiotensin converting enzyme inhibitor is administered in single or divided doses of from about 0.1 to about 500 mg/one to four times daily and the drug that acts at serotonin receptors is administered in single or divided doses of from about 1 µg to about 200 mg/l to 4 times daily.

14. The method as defined in claim 1 wherein the angiotensin converting enzyme inhibitor is employed in a weight ratio to the drug that acts at serotonin receptors of within the range of from about 0.002:1 to about $25 \times 10^4$:1.

* * * * *

UNITED STATES PATENT AND TRADEMARK OFFICE
CERTIFICATE OF CORRECTION

PATENT NO. : 5,032,578

DATED : July 16, 1991

INVENTOR(S) : Zola P. Horovitz

It is certified that error appears in the above-identified patent and that said Letters Patent is hereby corrected as shown below:

Column 8, line 24, please replace "(S)-1-L-pro" with
--(S)-1-[6-amino-2-[[hydroxy-(4-phenylbutyl)phosphinyl]oxy]-
1-oxohexyl]-L-pro- --.

Signed and Sealed this

Twenty-second Day of December, 1992

Attest:

DOUGLAS B. COMER

Attesting Officer

Acting Commissioner of Patents and Trademarks